United States Patent [19]
Huff

[11] 3,966,721
[45] June 29, 1976

[54] OXA- AND THIA-DIAZIN-2-ONES
[75] Inventor: Roger K. Huff, Wokingham, England
[73] Assignee: Ciba-Geigy Corporation, Ardsley, N.Y.
[22] Filed: Dec. 13, 1974
[21] Appl. No.: 532,433

[30] Foreign Application Priority Data
Dec. 19, 1973 Switzerland.................... 17810/73

[52] U.S. Cl. .................... 260/243 R; 260/244 R; 424/246; 424/248
[51] Int. Cl.² ............... C07D 285/34; C07D 273/04
[58] Field of Search .................... 260/243 R, 244 R

[56]       References Cited
       UNITED STATES PATENTS
3,859,299   1/1975   Hocker et al. .................... 260/244

Primary Examiner—John M. Ford
Attorney, Agent, or Firm—Harry Falber; Frederick H. Rabin

[57] ABSTRACT

Substituted 6-phenyl-oxa(thia)-diazin-6-one derivatives according to the formulae Ia and Ib described hereinafter are very effective coccidiostatics and selective herbicides.

16 Claims, No Drawings

OXA- AND THIA-DIAZIN-2-ONES

The present invention provides novel diazine derivatives, a process for their manufacture and also compositions which contain these compounds and a method of combating both coccidia and weeds which comprises the use of the novel diazine derivatives as active substances.

The novel diazine derivatives have the following formulae:

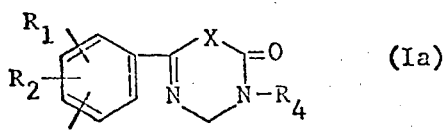

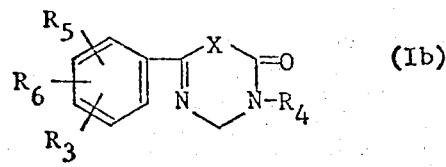

wherein X represents oxygen or sulphur, $R_1$ represents hydrogen, halogen, nitro, cyano, alkyl, alkoxy, haloalkyl, haloalkoxy, alkenyl, alkenyloxy, alkylthio, haloalkylthio, haloalkenyloxy, alkoxycarbonyl, alkylsulphonyl, haloalkylsulphonyl, 4-nitrophenoxy, $R_2$ represents hydrogen, halogen, nitro, alkyl, alkoxy, $R_3$ represents hydrogen, halogen, alkyl, alkoxy, $R_4$ represents hydrogen, alkyl alkoxyalkyl, alkenyl or cycloalkyl which is optionally bound through a methylene or an ethylene bridge, $R_5$ represents amino, monoalkylamino or dialkylamino, isothiocyano, alkoxycarbonylamino, monoalkylureido, dialkylureido or monoalkylthioureido or dialkylthioureido, alkanoylamino, and $R_6$ represents hydrogen, halogen, alkyl, alkoxy, cyano, haloalkyl, haloalkoxy, alkenyl, alkenyloxy, haloalkenyloxy, alkoxycarbonyl, alkylsulphonyl.

In the formulae Ia and Ib, alkyl as substituent or as part of a substituent is to be understood as meaning straight-chain or branched radicals with 1 to 12 carbon atoms, preferably with 1 to 4 carbon atoms, for example methyl, ethyl, n-propyl, isopropyl, n-butyl, isobutyl, sec.butyl or tert.butyl as well as n-pentyl, n-hexyl, n-octyl, n-decyl, n-dodecyl and isomers thereof; and also, for example, methoxy, ethoxy, n-propoxy, isopropoxy, n-butoxy, isobutoxy, sec.butoxy, tert.butoxy as well as pentoxy, hexoxy, decyloxy and dodecyloxy; and further, for example, mono-, di and trifluoromethyl or mono-, di- and trichloromethyl, difluorochloromethyl, fluorodichloromethyl, difluoroethyl, pentafluoroethyl, bromomethyl, iodomethyl, α-or β-chloroethyl, α- or β-bromoethyl and higher halogenated alkyl radicals. The radicals cited hereinbefore are also examples of corresponding alkoxycarbonyl, alkylsulphonyl or haloalkylsulphonyl groups. The preferred haloalkyl and haloalkylsulphonyl radicals are trifluoromethyl and trifluoromethylsulphonyl respectively. Examples of haloalkoxy radicals are β-chloroethoxy, β-bromoethoxy, trichloromethoxy and trifluoromethoxy. Allyl or methallyl are possible for alkenyl as a substituent and as part of a substituent. Cycloalkyl radicals have 3 to 6 carbon atoms and can be bound through a methylene or an ethylene group and they can also carry methyl or ethyl as substituents. Preferred cycloalkyl radicals are cyclopropyl and cyclopropylmethyl. Examples of an alkoxyalkyl group are methoxyethyl, ethoxyethyl, methoxyprop-1-yl or methoxyprop-2-yl. Alkylamino groups have 1 to 5 carbon atoms. Dialkylamino groups can be substituted symmetrically or unsymmetrically and have 2 to 10 carbon atoms. Examples of these groups are: methylamine, ethylamine, isopropylamine, methylethylamine, methyl-n-propylamine, octylamine, ethylisobutylamine. Alkyl- or dialkyl(thio)ureido groups have 2 to 6 or 3 to 10 carbon atoms respectively. By halogen is meant fluorine, chlorine, bromine or iodine.

The preferred compounds for combating coccidosis are those of the formula Ia wherein X represents oxygen or sulphur, $R_1$ represents nitro, cyano, haloalkyl with 1 to 3 carbon atoms, alkoxycarbonyl with at most 5 carbon atoms, alkylsulphonyl with 1 to 6 carbon atoms haloalkylthio with 1 to 4 carbon atoms or haloalkylsulphonyl with 1 to 4 carbon atoms, $R_2$ represents hydrogen, halogen, nitro, alkyl with 1 to 12 carbon atoms or alkoxy with 1 to 12 carbon atoms, $R_3$ represents hydrogen, halogen, alkyl with 1 to 4 carbon atoms, alkoxy with 1 to 4 carbon atoms, and $R_4$ represents methyl, ethyl, n-propyl or isopropyl. Compounds having especially good activity are those of the formula Ia wherein X represents oxygen or sulphur, $R_1$ represents nitro, cyano, trichloromethyl, trifluoromethyl, alkoxycarbonyl with 2 to 5 carbon atoms, alkylsulphonyl with 1 to 4 carbon atoms or trihalomethylsulphonyl, $R_2$ represents hydrogen, halogen, nitro or alkyl with 1 to 4 carbon atoms, $R_3$ represents hydrogen, halogen or alkyl with 1 to 4 carbon atoms and $R_4$ represents methyl or ethyl.

The novel diazine derivatives of the formula Ia are obtained by cyclising an amide of the formula II

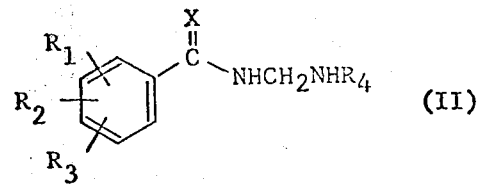

with phosgene in the presence of a base. Instead of phosgene, it is also possible to use carbonic acid dialkyl esters or haloformic esters, especially chloroformic esters, for the cyclisation reaction.

The alkyl esters with 1 to 4 carbon atoms are particularly suitable for the purpose.

Starting materials which are used for the manufacture of the novel diazine derivatives of the formula Ib are those of the formula Ia, wherein $R_1$ represents the nitro group and $R_2$ has a meaning other than nitro. The amino-diazine derivatives of the formula Ib which are characterised by the substituent $R_5=H_2N-$ are obtained by reduction and, if desired, these are reacted with a. an alkylisocyanate or
b. a compound of the formula III

R₇Y (III)

wherein R₇ represents dialkylcarbamoyl, alkanoyl, alkoxycarbonyl or alkyl and Y represents a halogen atom, or with c) a compound which is able to introduce the thiocarbonyl group (> C=S), optionally in the presence of a base. On using e.g. thiophosgene (CSCl₂) or phosgene and phosphorus pentasulphide, reaction d) results in the introduction of the isothiocyano group (SCN—), on using e.g. an alkylisothiocyanate in the introduction of the N-monoalkylureido group, and on using e.g. a dialkylthiocarbamoyl halide to the introduction of a N,N-dialkylthiocarbamoyl group for the substituent $R_5$.

On using e.g. a dialkylcarbamoyl halide, preferably the chloride, or phosgene and dialkylamine, reaction b) results in the introduction of a N,N-dialkylcarbamoyl group, on using e.g. an alkanecarboxylic halide in the introduction of an alkanoyl group, on using e.g. a halocarbonic acid alkyl ester in the introduction of the alkoxycarbonal group, and on using an alkyl halide in the introduction of an alkyl group for the substituent $R_5$. Reaction a) describes the introduction of a monoalkylureido group for the substituent $R_5$ by reaction of the amino group with the corresponding alkylisocyanate.

All the above conversions described in a), b) and c) of a free amino group into another functional group are known and the expert is familiar with them.

The initial reduction of the nitro group to the amino group can also be effected by conventional methods, for example with catalytically activated hydrogen in the presence of metal catalysts, e.g. raney nickel, palladium etc., with nascent hydrogen using base metals and acids, with stannous salts in acid solution etc. Preferably, the reduction is carried out with catalytically activated hydrogen.

The cyclisation is preferably carried out by treating the amide of the formula II at temperatures between −10°C and +10°C with phosgene in the presence of a solvent or diluent which is inert to the reactants and subsequently effecting the closure in the presence of a base at temperatures between 60°C and 120°C, if desired under pressure.

Suitable solvents or diluents are aliphatic or aromatic hydrocarbons, e.g. benzene, toluene, xylene, hexane; halogenated hydrocarbons, e.g. chloroform, methylene chloride; ketones, e.g. acetone, methyl ethyl ketone; nitriles, e.g. acetonitrile; but especially ethers and ethereal compounds, e.g. dialkyl ethers, dioxan, tetrahydrofuran, 1,2-dimethoxyethane. Suitable bases are especially tertiary amines, e.g. trialkylamines, pyridine or pyridine bases.

The amides of formula II used as starting materials are known. According to this process, an amide of the formula IV

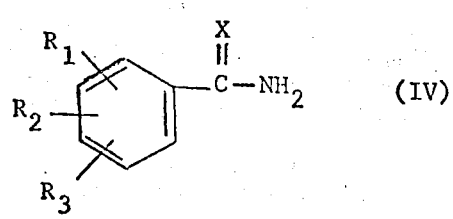

is reacted in the presence of an anhydrous organic or inorganic (e.g. HCl), at temperatures between −40°C and +30°C in a non-nucleophilic organic solvent which is fluid under the reaction conditions, with a hexahydro-s-triazine of the formula V

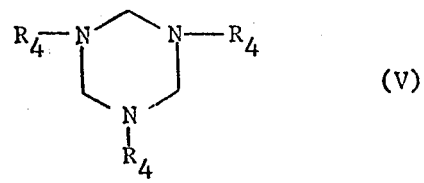

whereas aminomethylation occurs. The substituents $R_1$, $R_2$, $R_3$, $R_4$ and X have the meanings assigned to them in formula I. The intermediates which occur as salts of the acid employed are converted into the free amides of the formula II with bases.

According to another method which is described in Chem. Pharm. Bull. 21, (12) pp. 2775–2778 [1973], compounds of the formula II are also obtained by simultaneous reaction of compounds of the formula IV with formaldehyde and the amine hydrochloride $R_4$-$NH_2$·HCl in aqueous alcohol solution. In this process too, the intermediates of the formula II occur as salts (hydrochlorides) and are converted into the free amides by addition of a base.

The following Examples illustrate the invention. The Examples are followed by a Table in which those compounds are listed which are obtained in analogous manner.

EXAMPLE 1

A suspension of 21.5 g of N-(ethylaminomethyl)-benzamide hydrochloride (0.1 mole) in 300 ml of water is neutralised at 0°–25°C with 50 ml of 2 normal sodium hydroxide solution (0.1 mole). Extraction is performed with ethyl acetate, the organic phase is dried over magnesium sulphate and the solvent is evaporated off. The residue is taken up in 150 ml of tetrahydrofuran and the solution is treated dropwise with 9.9 g of phosgene (0.1 mole) in 150 ml of tetrahydrofuran. The addition is effected at 0°–25°C over the course of 1 hour. Then a solution of 15.8 g (0.2 mole) of pyridine in 150 ml of tetrahydrofuran is added over the course of a further hour. Stirring of the reaction mixture is continued for 2 hours and it is then refluxed for 3 hours. After the reaction mixture has cooled, the precipitate which has formed is filtered off and the filtrate is evaporated to dryness. The residue is taken up in chloroform and washed first with sodium bicarbonate solution and then with water. The solvent is evaporated off and crystallisation of the residue from ethyl acetate/n-hexane yields 6-phenyl-3-ethyl-3,4-dihydro-2H-1,3,5-oxadiazin-2-one with a melting point of 96°–98°C (compound 1).

EXAMPLE 2 a. A suspension of 24.6 g (0.1 mole) of N-(methylaminomethyl)-4-nitro-benzamide in 300 ml of water is neutralised at 0°–25°C with 50 ml of 2 normal sodium hydroxide solution (0.1 mole). The neutralised product is filtered off and dried in vacuo. It is then taken up in 150 ml of 1,2-dimethoxyethane and this solution is treated at 0°–25°C over the course of 1 hour with 9.9 g (0.1 mole) of phosgene in 150 ml of 1,2- dimethoxyethane. A solution of 15.8 g (0.2 mole) of pyridine in 150 ml of 1,2-dimethoxyethane is then added over the course of a further hour. Stirring of the reaction mixture is continued for 2 hours and then it is refluxed for 5 hours. After the reaction mixture has cooled, the precipitate which has formed is collected by filtration, the residue is dissolved in methylene chloride and washed first with sodium bicarbonate solution and then with water and dried. The solvent is evaporated and the residue is recrystallised from ethyl acetate to yield 6-(4-nitro-phenyl)-3-methyl-3,4-dihydro-2H-1,3,5-oxadiazin-2-one with a melting point of 153°–154°C (compound 2).

b. 3 g of 6-(4-nitro-phenyl)-3-methyl-3,4-dihydro-2H-1,3,5-oxadiazin-2-one in 60 ml of dioxan are hydrogenated with 0.3 g of platinum/charcoal (5%) as catalyst until the uptake of hydrogen has ceased. The hydrogenation is carried out at room temperature and under normal pressure. The catalyst is then filtered off, the solvent evaporated off in vacuo and the residue is recrystallised from ethyl acetate to yield 6-(4-amino-phenyl)-3-methyl,3,4-dihydro-2H-1,3,5-oxadiazin-2-one which melts at 173°–174°C with decomposition (compound 83).

EXAMPLE 3

5 g of N-(ethylaminomethyl)-thiobenzamide hydrochloride are suspended in 100 ml of water and the suspension is cooled to 0°C. Then 11.3 ml of 2 normal sodium hydroxide solution are added dropwise thereto and extraction is subsequently effected with ethyl acetate. The extract is dried over magnesium sulphate and the solvent is evaporated off. A solution of 10g of the residue in 100 ml of tetrahydrofuran is added dropwise to a solution of 8.2 g of phosgene in 100 ml of tetrahydrofuran which has been cooled with an ice/water mixture. Then 13 g of pyridine are slowly added and the mixture is allowed to warm to room temperature. Stirring is continued for 3 hours and then for another 3 hours under reflux. The precipitate which has formed is filtered off and the solvent is evaporated of in vacuo. The residue is purified through a silica gel column with methylene chloride/benzene 1:1 as eluant. The resultant 6-phenyl-3-ethyl-3,4-dihydro-2H-thiadiazin-2-one is a wax-like substance which melts at low temperatures (referred to in the Table as compound 3).

| Nr. | Compounds | Melting point in °C |
|---|---|---|
| 3 | 6-phenyl-3-ethyl-3,4-dihydro-2H-1,3,5-thiadiazin-2-one | wax |
| 4 | 6-(2,6-dichloro-phenyl)-3-ethyl-3,4-dihydro-2H-1,3,5-oxadiazin-2-one | 107°–108° |
| 5 | 6-(4-chlor-phenyl)-3-methyl-3,4-dihydro-2H-1,3,5-oxadiazin-2-one | 148°–149° |
| 6 | 6-(2,4-dichloro-phenyl)-3-isopropyl-3,4-dihydro-2H-1,3,5-oxadiazin-2-one | 61°–62° |
| 7 | 6-(4-chloro-phenyl)-3-isopropyl-3,4-dihydro-2H-1,3,5-oxadiazin-2-one | 80°–82° |
| 8 | 6-(4-methyl-phenyl)-3-isopropyl-3,4-dihydro-2H-1,3,5-oxadiazin-2-one | 86°–88° |
| 9 | 6-(3,4-dichloro-phenyl)-3-isopropyl-3,4-dihydro-2H-1,3,5-oxadiazin-2-one | 138°–140° |
| 10 | 6-(3,4-dichloro-phenyl)-3-methyl-3,4-dihydro-2H-1,3,5-oxadiazin-2-one | 154°–156° |
| 11 | 6-(4-methyl-phenyl)-3-methyl-3,4-dihydro-2H-1,3,5-oxadiazin-2-one | 166°–168° |
| 12 | 6-(4-nitro-phenyl)-3-ethyl-3,4-dihydro-2H-1,3,5-oxadiazin-2-one | 142°–144° |
| 13 | 6-(2,4-dichloro-phenyl)-3-methyl-3,4-dihydro-2H-1,3,5-oxadiazin-2-one | 86°–88° |
| 14 | 6-(3-trifluoromethyl-phenyl)-3-methyl-3,4-dihydro-2H-1,3,5-oxadiazin-2-one | 95°–97° |
| 15 | 6-(4-nitro-phenyl)-3-isopropyl-3,4-dihydro-2H-1,3,5-oxadiazin-2-one | 146°–148° |
| 16 | 6-(3-nitro-phenyl)-3-methyl-3,4-dihydro-2H-1,3,5-oxadiazin-2-one | 138°–140° |
| 17 | 6-(3,5-dinitro-phenyl)-3-methyl-3,4-dihydro-2H-1,3,5-oxadiazin-2-one | 134°–136° |
| 18 | 6-(2-chloro-4-nitro-phenyl)-3-methyl-3,4-dihydro-2H-1,3,5-oxadiazin-2-one | 113°–115° |
| 19 | 6-(4-cyano-phenyl)-3-methyl-3,4-dihydro-2H-1,3,5-oxadiazin-2-one | 192°–194° |
| 20 | 6-(4-methoxycarbonyl-phenyl)-3-methyl-3,4-dihydro-2H-1,3,5-oxadiazin-2-one | 207°–208° |
| 21 | 6-(4-nitro-phenyl)-3-n-decyl-3,4-dihydro-2H-1,3,5-oxadiazin-2-one | |
| 22 | 6-(4-trifluoromethyl-phenyl)-3-methyl-3,4-dihydro-2H-1,3,5-oxadiazin-2-one | 116°–118° |
| 23 | 6-(4-fluoro-phenyl)-3-methyl-3,4-dihydro-2H-1,3,5-oxadiazin-2-one | 131°–132° |
| 24 | 6-(3-nitro-4-chloro-phenyl)-3-methyl-3,4-dihydro-2H-1,3,5-oxadiazin-2-one | 142°–143° |
| 25 | 6-(4-tert.butyl-phenyl)-3-methyl-3,4-dihydro-2H-1,3,5-oxadiazin-2-one | 117°–118° |
| 26 | 6-(2,4-dinitro-phenyl)-3-methyl-3,4-dihydro-2H-1,3,5-oxadiazin-2-one | 142°–143° |
| 27 | 6-(3,4-dimethyl-phenyl)-3-methyl-3,4-dihydro-2H-1,3,5-oxadiazin-2-one | 128°–129° |
| 28 | 6-(4-methoxy-phenyl)-3-methyl-3,4-dihydro-2H-1,3,5-oxadiazin-2-one | 133°–134° |
| 29 | 6-(2-nitro-phenyl)-3-methyl-3,4-dihydro-2H-1,3,5-oxadiazin-2-one | |
| 30 | 6-(3-nitro-5-trifluoromethyl-phenyl)-3-methyl-3,4-dihydro-2H-1,3,5-oxadiazin-2-one | 125°–127° |
| 31 | 6-(3,5-dichloro-phenyl)-3-methyl-3,4-dihydro-2H-1,3,5-oxadiazin-2-one | 111°–112° |
| 32 | 6-(3-dinitro-phenyl)-3-methyl-3,4-dihydro-2H-1,3,5-oxadiazin-2-one | 142°–144° |
| 33 | 6-(2-methyl-4-nitro-phenyl)-3-methyl-3,4-dihydro-2H-1,3,5-oxadiazin-2-one | 131°–133° |
| 34 | 6-(3-methyl-4-nitro-phenyl)-3-methyl-3,4-dihydro-2H-1,3,5-oxadiazin-2-one | 155°–157° |
| 35 | 6-(3,4,5-triiodo-phenyl)-3-methyl-3,4-dihydro-2H-1,3,5-oxadiazin-2-one | |
| 36 | 6-[3,4,5-tris-(methoxy)-phenyl]-3-methyl-3,4-dihydro-2H-1,3,5-oxadiazin-2-one | 132°–133° |
| 37 | 6-(4-chloro-phenyl)-3-methoxyethyl-3,4-dihydro-2H-1,3,5-oxadiazin-2-one | 76°–78° |
| 38 | 6-(4-chloro-phenyl)-3-allyl-3,4-dihydro-2H-1,3,5-oxadiazin-2-one | 90°–92° |
| 39 | 6-(4-methoxycarbonylaminophenyl)-3-methyl-3,4-dihydro-2H-1,3,5-oxadiazin-2-one | |
| 40 | 6-(4-bromo-phenyl)-3-methyl-3,4-dihydro-2H-1,3,5-oxadiazin-2-one | 179°–180° |
| 41 | 6-(2,4-dimethyl-phenyl)-3-methyl-3,4-dihydro-2H-1,3,5-oxadiazin-2-one | 93°–94° |
| 42 | 6-[3,4,5-tris-(methoxy)-phenyl]-3-methyl-3,4-dihydro-2H-1,3,5-thiadiazin-2-one | |
| 43 | 6-(3-methoxy-phenyl)-3-methyl-3,4-dihydro-2H-1,3,5-oxadiazin-2-one | 149°–151° |
| 44 | 6-[3,4-bis-(methoxy)-phenyl]-3-methyl-3,4-dihydro-2H-1,3,5-oxadiazin-2-one | 143°–145° |
| 45 | 6-(2,4,6-trimethyl-phenyl)-3-methyl-3,4-dihydro-2H-1,3,5-oxadiazin-2-one | |
| 46 | 6-(4-ethoxy-phenyl)-3-methyl-3,4-dihydro-2H-1,3,5-oxadiazin-2-one | 127°–128° |
| 47 | 6-(2-ethoxy-phenyl)-3-methyl-3,4-dihydro-2H-1,3,5-oxadiazin-2-one | 84°–87° |
| 48 | 6-(2-chloromethyl-phenyl)-3-methyl-3,4-dihydro-2H-1,3,5-oxadiazin-2-one | |
| 49 | 6-(4-methylsulphonyl-phenyl)-3-methyl-3,4-dihydro-2H-1,3,5-oxadiazin-2-one | 207°–209° |
| 50 | 6-(3,5-dinitro-2-methyl-phenyl)-3-methyl-3,4-dihydro-2H-1,3,5-oxadiazin-2-one | 112°–114° |
| 51 | 6-(2-fluoro-4-nitro-phenyl)-3-methyl-3,4-dihydro-2H-1,3,5-oxadiazin-2-one | 167° |
| 52 | 6-(3-fluoro-4-nitro-phenyl)-3-methyl-3,4-dihydro-2H-1,3,5-oxadiazin-2-one | 117°–118° |
| 53 | 6-(2-bromo-4-nitro-phenyl)-3-methyl-3,4-dihydro-2H-1,3,5-oxadiazin-2-one | 122°–123° |
| 54 | 6-[4-(4'-nitrophenoxi)-phenyl]-3-methyl-3,4-dihydro-2H-1,3,5-oxadiazin-2-one | 170°–173° |
| 55 | 6-(4-trifluoromethylsulphonyl- | 183°–184° |

-continued

| Nr. | Compounds | Melting point in °C |
|---|---|---|
| | phenyl)-3-methyl-3,4-dihydro-2H-1,3,5-oxadiazin-2-one | |
| 56 | 6-phenyl-3-methyl-3,4-dihydro-2H-1,3,5-oxadiazin-2-one | 133°–135° |
| 57 | 6-(4- ethylsulphonyl-phenyl)-3-methyl-3,4-dihydro-2H-1,3,5-oxadiazin-2-one | 175°–177° |
| 58 | 6-(4-isopropylsulphonyl-phenyl)-3-methyl-3,4-dihydro-2H-1,3,5-oxadiazin-2-one | 174°–177° |
| 59 | 6-(4-n-butylsulphonyl-phenyl)-3-methyl-3,4-dihydro-2H-1,3,5-oxadiazin-2-one | 156°–158° |
| 60 | 6-(4-chloro-3-trifluoromethyl-phenyl)-3-methyl-3,4-dihydro-2H-1,3,5-oxadiazin-2-one | |
| 61 | 6-(3-chloro-4-nitro-phenyl)-3-methyl-3,4-dihydro-2H-1,3,5-oxadiazin-2-one | 139°–140° |
| 62 | 6-[3,5-bis(trifluoromethyl)-phenyl]-3-methyl-3,4-dihydro-2H-1,3,5-oxadiazin-2-one | |
| 63 | 6-(4-methylthio-phenyl)-3-methyl-3,4-dihydro-2H-1,3,5-oxadiazin-2-one | 143°–145° |
| 64 | 6-(4-trifluormethylthio-phenyl)-3-methyl-3,4-dihydro-2H-1,3,5-oxadiazin-2-one | |
| 65 | 6-(4-trichloromethylsulfonyl-phenyl)-3-methyl-3,4-dihydro-2H-1,3,5-oxadiazin-2-one | |
| 66 | 6-(2-nitro-4-chlor-phenyl)-3-methyl-3,4-dihydro-2H-1,3,5-oxadiazin-2-one | |
| 67 | 6-(3-bromo-4-methylsulfonyl-phenyl)-3-methyl-3,4-dihydro-2H-1,3,5-oxadiazin-2-on | |
| 68 | 6-(4-methylsulphonyl-phenyl)-3-ethyl-3,4-dihydro-2H-1,3,5-oxadiazin-2-one | 209°–212° |
| 69 | 6-(4-methylsulphonyl-phenyl)-3-cyclopropyl——3,4-dihydro-2H-1,3,5-oxadiazin-2-one | 195°–198° |
| 70 | 6-(3,5-dinitro-phenyl)-3-methyl-3,4-dihydro-2H-1,3,5-thiadiazin-2-one | |
| 71 | 6-(2-chloro-4-nitro-phenyl)-3-methyl-3,4-dihydro-2H-1,3,5-thiadiazin-2-one | |
| 72 | 6-(4-methylsulphonyl-phenyl)-3-methyl-3,4-dihydro-2H-1,3,5-thiadiazin-2-one | |
| 73 | 6-(3,5-ninitro-2-methyl-phenyl)-3-methyl-3,4-dihydro-2H-1,3,5-thiadiazin-2-one | |
| 74 | 6-(4-trifluoromethylsulfonyl-phenyl)-3-methyl-3,4-dihydro-2H-1,3,5-thiadiazin-2-one | |
| 75 | 6-(4-ethylsulphonyl-phenyl)-3-methyl-3,4-dihydro-2H-1,3,5-thiadiazin-2-one | |
| 76 | 6-(2-nitro-4-chloro-phenyl)-3-methyl-3,4-dihydro-2H-1,3,5-thiadiazin-2-one | |
| 77 | 6-(4-methylsulphonyl-phenyl)-3-athyl-3,4-dihydro-2H-1,3,5-thiadiazin-2-one | |
| 78 | 6-(4-methylsulfonyl-2-chlor-phenyl)-3-methyl-3,4-dihydro-2H-1,3,5-oxadiazin-2-one | |
| 79 | 6-(4-chloro-phenyl)-3-cyclopropyl-3,4-dihydro-2H-1,3,5-oxadiazin-2-one | 135°–137° |
| 80 | 6-(4-β-chloroallyloxy-2-nitro-phenyl)-3-methyl-3,4-dihydro-2H-1,3,5-oxadiazin-2-one | |
| 81 | 6-(3-chloro-4-cyano-phenyl)-3-methyl-3,4-dihydro-2H-1,3,5-oxadiazin-2-one | |
| 82 | 6-(4-amino-phenyl)-3-methyl-3,4-yl-3,4-dihydro-2H-1,3,5-oxadiazin-2-one | |
| 83 | 6-(4-amino-phenyl)-3-methyl-3,4-dihydro-2H-1,3,5-oxadiazin-2-one | 173°–174° |

As mentioned already, the novel diazine derivatives of the formula Ia are used preferably for combating coccidiosis in poultry.

Coccidiosis is the most widely occurring disease that attacks poultry. It is caused by protozoa of the genus Eimeria, e.g. Eimeria tenella, Eimeria brunetti, Eimeria maxima, Eimeria necatrix, Eimeria acervulina etc. Animals attacked by Coccidia gain poorly in weight, are subject to intestinal bleeding and their excreta contains blood. In cases of severe infection, the coccidiosis results in a high mortality rate in poultry. It is known that compounds with coccidiostatic action which are available as commercial products lead within a short period of time to the build-up of resistance in the parasites. It is therefore a matter of the greatest concern to the poultry breeder that new compounds suitable for combating and preventing this disease be developed.

The coccidiostatic action of the diazine derivatives of the formulae Ia and Ib are illustrated in the following test.

TESTS CARRIED OUT ON HENS INFECTED WITH EIMERIA TENELLA

Ten 8 day old chicks are infected with 80.000 sporulated oocysts of Eimeria tenella. Medicated chicken feed containing 400 ppm of active substance is administered freely for 3 days before and over the course of 10 days after the infection. The chicks are dissected at the conclusion of the test. Each of the control groups consists of 10 untreated, uninfected chicks and 10 untreated and infected chicks. The amount of active substance consumed per group is ascertained by re-weighing the feed. Mortality, weight increase, condition of the appendices as well as elimination of oocysts in comparison with the two control groups serve as activity paramaters.

The following active substances inhibited attack by coccidiosis in infected chicks particularly effectively, i.e. in the corresponding test group there occured no mortalities
no appendix lesions and
no elimination of oocysts and the state of health and weight increase of the test subjects achieved approximately the level of the uninfected and untreated control group: compounds 18, 18, 19, 49, 50, 55, 57, 58, 59, 60, 62, 66, 67, 68, 69, 70, 71, 72, 73, 74, 75, 76, 77, 78, 79 and 81.

The active substances were tolerated by the chicks without any symptoms.

Elimination of oocysts occurred in the case of the infected untreated control chicks. Severe appendix lesions were observed. The mortality rate was 20%.

The manufacture of coccidiostatic compositions is effected in known manner by intimately mixing and grinding active substances of the formula Ia or Ib with suitable carriers, optionally with the addition of dispersants or solvents which are inert to the active substances. The active substances can take the form of and be applied in the following processed forms:

SOLID FORMS:

dusts, granules, coated granules, impregnated granules and homogeneous granules;

ACTIVE SUBSTANCE CONCENTRATES WHICH ARE DISPERSIBLE IN WATER powder mixes

LIQUID PROCESSED FORMS solutions, pastes (emulsions).

The particle size of the carrier materials for dust and powder mixes is desirably up to about 0.1 mm and for granules 10—500µ (0.001 - 0.5 nm).

Coccidiostatic compositions are preferably in the form of feed concentrates. Examples of carriers for such concentrates are high-protein feeds, coarse grains or protein concentrates. In addition to the active substances, such feed concentrates can contain additives, vitamins, antibiotics, chemotheuropeutic agents or other pesticides, principally bacteriostatic agents, fungistatic agents, anthelmintic agents, coccodiostatic agents or also hormone preparations, substances with anabolic activity or other substances which promote growth, improve the quality of the flesh of animals for slaughtering or which in some other way are beneficial to the organism.

FEED CONCENTRATES

The following feed mixes are used to manufacture 6 kg of final feed with a) 25 ppm, b) 50 ppm, c) 200 ppm and d) 400 ppm:

a. 0.15 part by weight of a compound according to formula Ia or Ib, 49.85 parts by weight of bolus alba 150.0 parts by weight of standard poultry feed;
b. 0.30 part by weight of a compound according to formula Ia or Ib 49.70 parts by weight of bolus alba 5.0 parts by weight of silicic acid 150.0 parts by weight of standard poultry feed;
c. 1.2 parts by weight of a compound according to formula Ia or Ib 43.8 parts by weight of bolus alba 5.0 parts by weight of silicic acid 150.0 parts by weight of standard poultry feed;
d. 2.4 parts by weight of a compound according to formula Ia or Ib 47.6 parts by weight of bolus alba 150.0 parts by weight of standard poultry feed.

The auxiliary feed according to the invention is either mixed direct with the carriers or e.g. applied to the carriers dissolved in chloroform. The mix is subsequently ground to the desired particle size of e.g. 5–10µ. These premixes are mixed with 5800 parts by weight of standard feed or processed to 6000 parts by weight of swill. Furthermore, these premixes can be tabletted to 6000 parts by weight of standard feed (feed pellets).

The diazine derivatives of the formula I also possess herbicidal properties and are suitable in particular for combating grass-like and broad-leaved weeds. When used in high concentrations, the novel compounds act as total herbicides; when used in low concentrations they act as selective herbicides. Deep rooted, difficultly controllable annual and perennial weeds are successfully impaired in their growth or destroyed by the active substances of the formula I. The novel active substances can be applied with the same good success before germination (*preemergence*) and after germination (*postemergence*). Thus meadow weeds, for example millet species (*Panicum sp.*) mustard species (*Sinapis sp.*) pigweed (*Chenopodiacease*), *foxtail species* (*Amaranthus sp.*), grasses (*Lolium sp.*), compositae (*Taraxacum sp.*), camomile species (*Matricaria sp.*), are destroyed or inhibited in their growth without damage being caused to cultivated plants, such as cereals, maize, cotton, sorghum, soya beans etc.

Varieties of weeds which are difficult to control in rice cultures are also attacked and destroyed by these active substances, for example in cultures of water rice Echinochloa sp., Eleocharis sp., Panicum sp., Cyperaceen, Paspalum sp., etc.; and in cultures of dry rice Echinochloa sp., Digitaria sp., Brachiaria sp., Sida sp., Cyperaceen, Acanthosperum sp., etc. Since the active substances kill the plants gradually and therefore have no obviously deleterious effect on the oxygen balance and the balance of nature, they are very suitable for application in cultures of water rice. Furthermore, the active substances have a broad activity spectrum against a variety of aquatic weeds, e.g. emersed plants, aquatic plants with and without floating leaves, underwater water plants, algae etc.

The rates of application vary and depend on the time of application. They are between 0.1 to 10 kg of active substance per hectare: in preemergence application up to 4 kg of active substance per hectare and in postemergence application from 1 to 5 kg per hectare. In order to totally destroy entire crops of weeds, for example on fallow land neighbouring on the cultivated areas, it is necessary to use more than 10 kg of active substance per hectare. The normal crop rotation may proceed on application of the novel active substances without any detrimental effects.

Diazine derivatives which have proved particularly effective are those of the restricted formula Ia

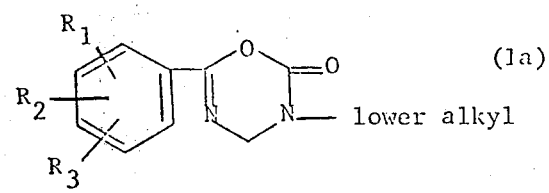

wherein $R_1$, $R_2$ and $R_3$ have the meanings assigned to them in formula Ia. They are used in plant cultures such as cotton, cereals, soyam, sugar beet, rice. Compound 10 selectively controls weeds, especially in rice, and compound 14 in rice, cotton and sugar beet. Compound 31 is particularly suitable for controlling perennial grasses. The use of compound No. 13 results in an excellent weed control, especially in crop cultures such as sugar beet and rice which are well tolerated.

The herbicidal compositions are manufactured in known manner by intimately mixing and grinding active substances of the general formulae Ia and Ib with suitable carriers, optionally with the addition of dispersants or solvents which are inert to the active substances. The active substances can take and be used in the following processed forms:

SOLID FORMS dusts, tracking agents, granules, coated granules, impregnated granules and homogeneous granules;

ACTIVE SUBSTANCE CONCENTRATES WHICH ARE DISPERSIBLE IN WATER wettable powders, pastes, emulsions;

LIQUID FORMS solutions.

It is possible to mix other active substances or compositions with these herbicidal compositions, for example, insectidides, fungicides, bactericides, fungistatic agents, bacteriostatic agents or nematocides in order to broaden the activity spectrum. The compositions according to the invention can contain in addition plant fertilizers, trace elements etc.

Processed forms of the novel active substances of the general formulae Ia and Ib are described hereinbelow. Parts denote parts by weight.

WETTABLE POWDER

The following constituents are used to manufacture a 40% wettable powder:
- 40 parts of an active substance of the formula Ia or Ib
- 5 parts of the sodium salt of ligninsulphonic acid
- 1 parts of the sodium salt of dibutylnaphthalenesulphonic acid
- 54 parts of silicic acid.

The active substance is intimately mixed in suitable mixing devices with the additives and the mix is ground in corresponding mills and rollers. A wettable powder is obtained which can be diluted with water to give suspensions of any desired concentration.

EMULSION CONCENTRATES

The following substances are used to manufacture a 10% emulsion concentrate:
- 10 parts of an active substance of the formula Ia or Ib
- 3.4 parts of an epoxidised plant oil
- 13.4 parts of a combination emulsifier consisting of a fatty alcohol polyglycol ether and the calcium salt of alkylarylsulphonate
- 40 parts of dimethyl formamide
- 43.2 parts of xylene.

By diluting this concentrate with water it is possible to manufacture emulsions of any desired concentration.

I claim:

1. Diazine derivatives of the formulae Ia and Ib

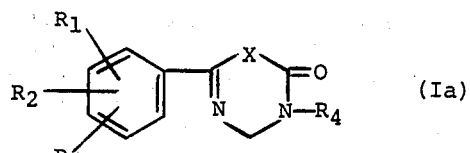

(Ia)

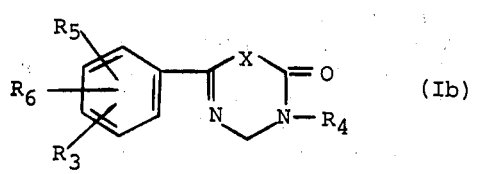

(Ib)

wherein X represents oxygen or sulphur, $R_1$ represents hydrogen, halogen, nitro, cyano, $C_1$–$C_{12}$ alkyl, $C_1$–$C_{12}$ alkoxy, $C_1$–$C_{12}$ haloalkyl, $C_1$–$C_{12}$ haloalkoxy, $C_3$–$C_4$ alkenyl, $C_3$–$C_4$ alkenyloxy, $C_1$–$C_{12}$ alkylthio, $C_1$–$C_{12}$ haloalkylthio, $C_3$–$C_4$ haloalkenyloxy, $C_1$–$C_{12}$ alkoxycarbonyl, $C_1$–$C_{12}$ alkylsulphonyl, $C_1$–$C_{12}$ haloalkylsulphonyl, 4-nitrophenoxy, $R_2$ represents hydrogen, halogen, nitro, $C_1$–$C_{12}$ alkyl, $C_1$–$C_{12}$ alkoxy, $R_3$ represents hydrogen, halogen, $C_1$–$C_{12}$ alkyl, $C_1$–$C_{12}$ alkoxy, $R_3$ represents hydrogen, halogen, $C_1$–$C_{12}$ alkyl, $C_1$–$C_{12}$ alkoxy, $R_4$ represents hydrogen, $C_1$–$C_{12}$ alkyl, $C_2$–$C_5$ alkoxyalkyl, $C_3$–$C_4$ alkenyl or $C_3$–$C_6$ cycloalkyl which is optionally bound through a methylene or an ethylene bridge, $R_5$ represents amino, $C_1$–$C_5$ monoalkylamino or $C_2$–$C_{10}$ dialkylamino, isothiocyano, $C_1$–$C_{12}$ alkoxycarbonylamino, $C_2$–$C_6$ monoalkylureido, $C_3$–$C_{10}$ dialkylureido or $C_2$–$C_6$ monoalkylthioureido or $C_3$–$C_{10}$ dialkylthioureido, $C_1$–$C_{12}$ alkanoylamino, and $R_6$ represents hydrogen, halogen, $C_1$–$C_{12}$ alkyl, $C_1$–$C_{12}$ alkoxy, cyano, $C_1$–$C_{12}$ haloalkyl, $C_3$–$C_4$ alkenyl, $C_3$–$C_4$ alkenyloxy, $C_3$–$C_4$ haloalkenyloxy, $C_1$–$C_{12}$ alkoxycarbonyl, $C_1$–$C_{12}$ alkylsulphonyl.

2. The diazine derivative of the formula Ia according to claim 1, wherein X represents oxygen and $R_4$ represents a lower alkyl radical with 1 to 4 carbon atoms.

3. The diazine derivative of the formula Ia according to claim 1, wherein X represents oxygen or sulphur, $R_1$ represents nitro, cyano, haloalkyl with 1 to 3 carbon atoms, alkoxycarbonyl with at most 5 carbon atoms, alkylsulphonyl with 1 to 6 carbon atoms, haloalkylthio or haloalkylsulphonyl with 1 to 4 carbon atoms, $R_2$ represents hydrogen, halogen, nitro, alkyl with 1 to 12 carbon atoms or alkoxy with 1 to 12 carbon atoms, $R_3$ represents hydrogen, halogen, nitro, alkyl with 1 to 4 carbon atoms or alkoxy with 1 to 4 carbon atoms, and $R_4$ represents methyl, ethyl, n-propyl or isopropyl.

4. The diazine derivative of the formula Ia according to claim 1, wherein X represents oxygen or sulphur, $R_1$ represents nitro, cyano, trichloromethyl, trifluoromethyl, alkoxycarbonyl with at most 5 carbon atoms, alkylsulphonyl with 1 to 4 carbon atoms or trihalomethylsulphonyl, $R_2$ represents hydrogen, halogen, nitro or alkyl with 1 to 4 carbon atoms, $R_3$ represents hydrogen, halogen or alkyl with 1 to 4 carbon atoms and $R_4$ represents methyl or ethyl.

5. 6-(2,4-dichloro-phenyl)-3-methyl-3,4-dihydro-2H-1,3,5-oxadiazin-2-one according to claim 1.

6. 6-(3,5-dinitro-phenyl)-3-methyl-3,4-dihydro-2H-1,3,5-oxadiazin-2-one according to claim 1.

7. 6-(2-chloro-4-nitro-phenyl)-3-methyl-3,4-dihydro-2H-1,3,5-oxadiazin-2-one according to claim 1.

8. 6-(4-cyano-phenyl)-3-methyl-3,4-dihydro-2H-1,3,5-oxadiazin-2-one according to claim 1.

9. 6-(4-methylsulphonyl-phenyl)-3-methyl-3,4-dihydro-2H-1,3,5-oxadiazin-2-one of the formula

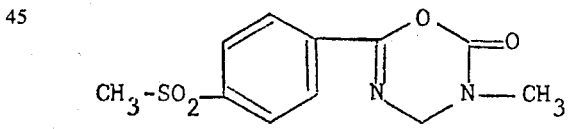

according to claim 1.

10. 6-(3,5-dinitro-2-methyl-phenyl)-3-methyl-3,4-dihydro-2H-1,3,5-oxadiazin-2-one according to claim 1.

11. 6-(4-trifluoromethylsulphonyl-phenyl)-3-methyl-3,4-dihydro-2H-1,3,5-oxadiazin-2-one according to claim 1.

12. 6-(4-ethylsulphonyl-phenyl)-3-methyl-3,4-dihydro-2H-1,3,5-oxadiazin-2-one according to claim 1.

13. 6-(4-methylsulphonyl-phenyl)-3-methyl-3,4-dihydro-2H-1,3,5-thiadiazin-2-one according to claim 1.

14. 6-(4-ethylsulphonyl-phenyl)-3-methyl-3,4-dihydro-2H-1,3,5-thiadiazin-2-one according to claim 1.

15. A process for the manufacture of diazine derivatives of the formula Ia, wherein an amide of the formula II

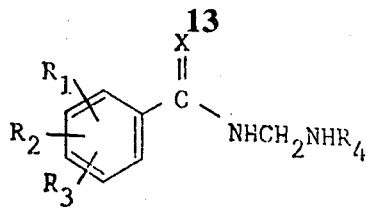

in which $R_1$ to $R_4$ and X have the meanings assigned to them in claim 1, is cyclised with phosgene, carbonic acid $C_1$–$C_4$ dialkyl esters or haloformic esters in the presence of a base.

16. A process according to claim 15, wherein the cyclisation is carried out with phosgene in the presence of an inert solvent or diluent in a temperature range of initially −10°C to +30°C and subsequently in the presence of a base between 60°C and 120°C.

* * * * *